(12) United States Patent
Gilmour

(10) Patent No.: US 6,287,268 B1
(45) Date of Patent: Sep. 11, 2001

(54) BRACE

(75) Inventor: Robert Farrer Gilmour, Auckland (NZ)

(73) Assignee: Bodyworks Properties Limited, Auckland (NZ)

( * ) Notice: Subject to any disclaimer, the term of this patent is extended or adjusted under 35 U.S.C. 154(b) by 0 days.

(21) Appl. No.: 09/344,363

(22) Filed: Jun. 25, 1999

(30) Foreign Application Priority Data

Jun. 25, 1998 (NZ) ...................................... 330789

(51) Int. Cl.[7] ................................ A61F 5/00; A61F 5/37
(52) U.S. Cl. ............................... 602/26; 602/16; 128/882
(58) Field of Search ..................... 602/5–6, 16, 23–26, 602/62, 20–21, 60–61; 128/882, 881, 878–879; 2/22, 24; 623/39–45, 59–60; D24/190

(56) References Cited

U.S. PATENT DOCUMENTS

| | | | | |
|---|---|---|---|---|
| D. 353,005 | * | 11/1994 | Glidden | D24/190 |
| 3,669,105 | * | 6/1972 | Castiglia | 602/16 |
| 4,381,768 | * | 5/1983 | Erichsen | 602/16 |
| 4,796,610 | * | 1/1989 | Cromartie | 602/26 |
| 4,805,606 | * | 2/1989 | McDavid, III | 128/80 C |
| 4,817,588 | * | 4/1989 | Bledsoe | 128/80 |
| 5,277,698 | * | 1/1994 | Taylor | 602/16 X |
| 5,383,845 | * | 1/1995 | Nebloln | 602/26 |
| 5,458,565 | * | 10/1995 | Tillinghast | 602/16 X |
| 5,823,931 | * | 10/1998 | Gilmour | 602/16 X |

* cited by examiner

Primary Examiner—Denise Pothier
(74) Attorney, Agent, or Firm—Young & Thompson

(57) ABSTRACT

A brace having a hinge and a pair of substantially oppositely extending arms extending outwardly from the hinge. A first attachment point is associated with a first one of the arms, and a second attachment point is associated with a second one of the arms, so that fixing elements can extend from the first attachment point to the second arm and from the second attachment point to the first arm. Each attachment point is constructed so that the first attachment point is spaced from the first arm and the second attachment point is spaced from the second arm, but so that during rotation of the hinge the first attachment point and second attachment point remain at a substantially constant distance from a selected point between the first and second attachment points.

3 Claims, 1 Drawing Sheet

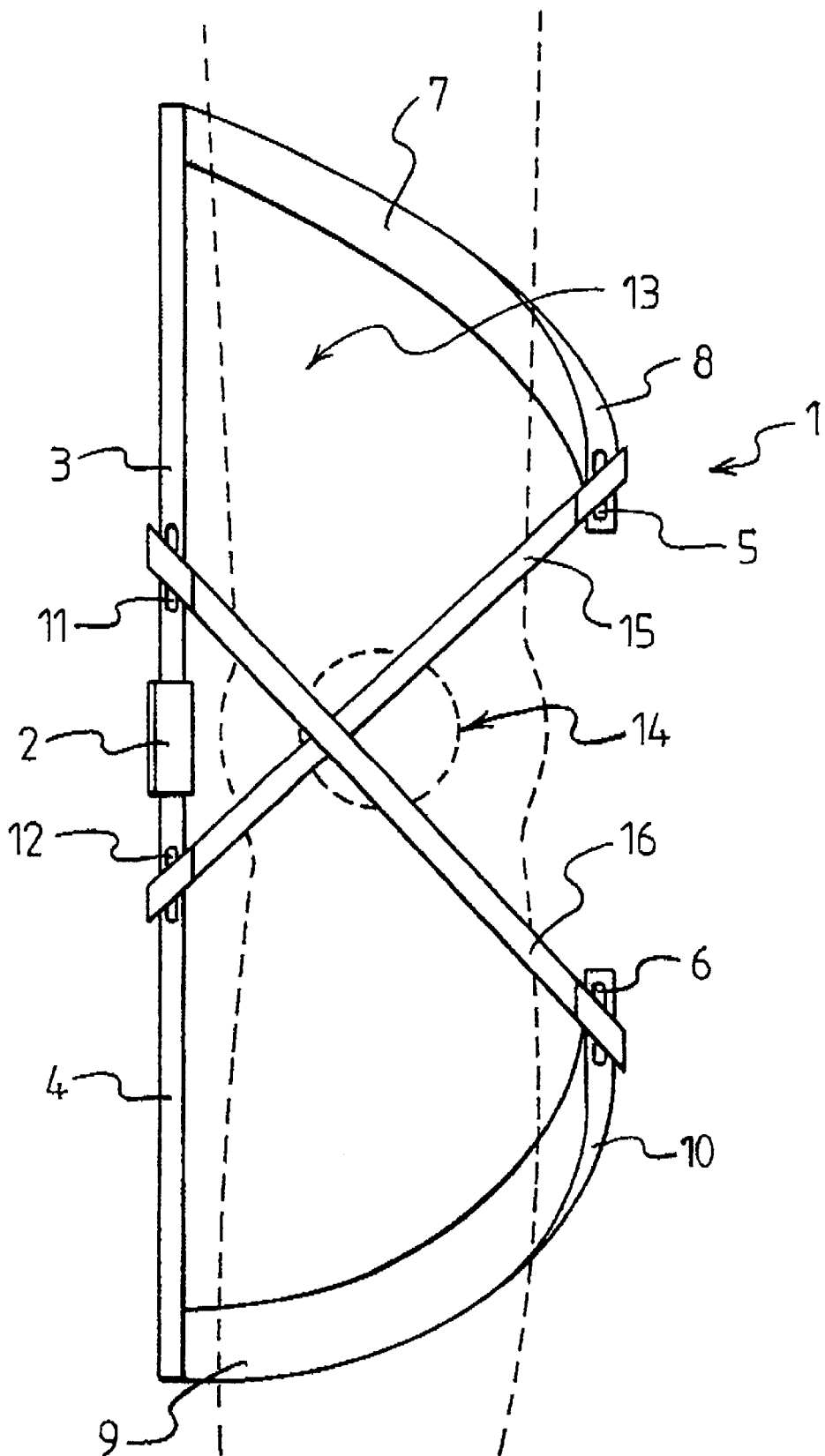

BRACE

This invention relates to a brace in particular relates to a brace for a body joint particularly but not necessarily solely a knee.

FIELD OF INVENTION

Currently available braces consist of braces which exert a varus or valgus force. There is some debate as to whether they manage to achieve this throughout gait or just at the initial and final phase of the gait which is to say that the varus and valgus forces are not applied during full weight bearing when the knee is extended (that is to say straight). There is some evidence to suggest that braces are unstable during this mid phase of the gait and therefore lose efficiency. Also there is no definite proof of efficacy during weight bearing. As the muscle changes shape during the progression of the gait changes in muscle shape can load up or unload the brace.

Braces can be single hinged braces or double hinged braces. The advantage of a single hinged brace is that such braces are more comfortable and also more easily absorb or accommodate any rotation of the lower leg relative to the upper leg during flexion. The disadvantage of single hinged braces is that when the leg changes shape during the mid phase of gait for example by way of changes in muscle shape, the braces tend to rotate on the muscle and therefore do not maintain the required corrective force.

In respect of double hinged braces they have the advantage that they exert a more constant force on the skeleton during gait because they are fitted against both sides of the leg, however double hinged braces have the disadvantage that they are heavy, less comfortable, and do not anticipate rotation of the lower leg. Such braces may drag across the soft tissue in many users.

It is therefore an object of the present invention to provide a brace which will obviate or minimise the foregoing disadvantages in a simple yet effective manner or which will at least provide the public with a useful choice.

SUMMARY OF INVENTION

Accordingly the invention consists in a brace comprising or including a hinge, a pair of substantially oppositely extending arms extending outwardly from the hinge, a first attachment point associated with a first one of said arms, and a second attachment point associated with a second one of said arms, first mounting means carrying the first attachment point and second mounting means carrying the second attachment point, each attachment point being constructed so that the first attachment point is spaced from the first arm and the second attachment point is spaced from the second arm, but so that during rotation of the hinge the first attachment point and second attachment point remain at a substantially constant distance from a selected point between the first and second attachment points.

Preferably during rotation as above said the first attachment point remains a substantially constant distance from the pivot axis of the hinge and the second attachment point remains a substantially constant distance from the pivot axis of the hinge.

Preferably each mounting means comprises an arm extending outwardly from the arm extending from the hinge, the mounting means arm ending with a part lying substantially parallel to the arm from which the mounting means arm extends, the parallel part of the mounting means arm carrying the attachment point.

Preferably the brace further includes fitting means to enable in use the brace to be fitted about the knee of the user.

Preferably the fitting means comprise a strap or the like fixing element extending from the first attachment point to the second arm and the further strap extending from the second attachment point to the first arm.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWING

The sole FIGURE represents a diagrammatic representation of a brace according to a preferred embodiment (attached to a knee, shown from the back of a leg).

DETAILED DESCRIPTION OF THE INVENTION

One preferred form of the invention will now be described with reference to the accompanying drawing which is a diagrammatic representation of a brace according to one preferred form of the invention.

In the preferred form of the invention a brace 1 is provided which has a hinge 2 and a pair of arms 3 and 4 extending outwardly therefrom. Such hinge constructions with arms extending outwardly are known in the art and any effective such construction can be used to form the basis of the construction described herein.

A first attachment point 5 is provided and a second attachment point 6 are provided. The attachment point 5 is associated with the first arm 3 and the second attachment point 6 is associated with the second arm 4. The attachment point may be positioned in each case by a mounting means which connects the attachment point 5 or 6 to the appropriate arm 3 or 4. Thus an outwardly extending arm 7 may extend outwardly from the first arm 3 terminating in a part 8 which lies substantially parallel to the arm 3 but is spaced therefrom. Similarly the attachment point 6 may be on an arm 9 extending outwardly from arm 4 and terminating in a part 10 which lies substantially parallel to arm 4 and carries the attachment point 6. The attachment points 5 and 6 could be loops or buckles formed on the parts 8 and 10 but any suitable attachment point construction can be used. Further connecting points are provided on the arms 3 and 4 and for example the connecting point on the arm 3 may be a loop 11 and the connecting point on the arm 4 may be a loop 12 or in each case any other suitable buckle or connecting arrangement may be used.

The arms 7 and 9 are shaped so that they will pass around the limb preferably the leg of a user indicated in dotted fashion at 13 and including a knee indicated at 14. The shape is such that movement of the brace 1 up and down along the leg is substantially prevented. Thus the arms 7 and 9 are angled downwardly and around. This can be achieved by forming the arms 7 and 9 into a spiral, the dimensions of which will depend on the size of the leg 13. The arms 7 and 9 formed so that movement of the arms in directions parallel to the leg are substantially prevented but some flexibility for movement transverse to the axis is allowed to assist in achieving optimum results in use.

Fitting means are provided, which could be suitable known bindings but in a preferred form of the invention the fitting means comprise straps 15 and 16. Strap 15 is connected between attachment point 5 and connecting point 12 and strap 16 is connected between attachment point 6 and connection point 11. In each case the straps may terminate in a manner to provide co-operating pads of looped material and hooks such as that sold by reference to the trade mark VELCRO.

The straps 15 and 16 in the preferred form in effect continue the spiral of arms 7 and 9. Thus in this embodiment the point 5 (when seen in plan) is at the apex of an isosceles triangle formed by arm 3, arm 7 and strap 15.

Use of the invention is as follows:

The brace 1 is positioned about a joint for example the knee 14 of a user. The arms 7 and 9 extend across the front of the leg. At the back of the brace 1 the straps 15 and 16 originating above and below the knee pass behind the knee, cross, and are attached to the connection points 11 and 12. Desirably the straps are tensioned to give ten to twenty degrees of flexion. Thus positioned the brace exerts the desired force during the initial and end phase of the gait and during the weight bearing phase when the leg is straight the straps tighten and increase the grip of the brace 1 on the leg 13. This maximises the efficiency of the force exerted by the brace 1. The straps 15 and 16 hold the attachment points 5 and 6 to either side of the leg in a substantially constant position and therefore the brace 1 remains stable and exerts a substantially constant force. The rigid elements that is to say the arms 7 and 9 and also the arms 3 and 4 are shaped to allow rotation of the soft tissue within the brace 1 but they hold the attachment points 5 and 6 in a substantially constant position relative to a position between the attachment points 5 and 6. This position is essentially the line of the knee joint, or more broadly is a constant position on a line parallel to the trochanter, knee, ankle (TKA) line. In effect a similar result is achieved as having a rigid bar with a hinge therein between the two attachment points as though a hinge arm were in position. In the construction if the straps are adjusted with the knee flexed then the stabilising force is increased when the leg is straightened. The brace creates a virtual hinge between attachment points 5 and 6 allowing the advantages of a double brace to be achieved.

However the particular strap configuration in conjunction with sideways flexibility of the arms 7 and 9 (if provided) increases the grip of the brace onto the leg in extension. That is to say, the straps tighten onto the leg because of muscle expansion as the legs of the user straighten. Thus at heel strike, which is a time of high pressure, the straps are at their tightest. Loosening of the straps during other times of the gait reduces risks of reducing or cutting off blood flow in the leg. Sideways flexing of the attachment points (if provided) assists the brace in self adjusting to changes in muscle profile.

Thus it can be seen that at least in the preferred form of the invention a brace is provided which allow advantages of a single brace to be achieved along with advantages of a double hinged brace but without the weight and lack of comfort of the double hinged brace. Tendencies to drag across the soft tissue of the wearer is reduced.

What I claim is:

1. A brace for surrounding a leg of a user comprising:

a first arm and a second arm forming a pair of substantially oppositely extending arms extending from a hinge, the first and second arms adapted to lie on a first side of a user's leg;

a first mounting means including a third arm angled and extending from the first arm, the third angled arm ending with a first part lying substantially parallel to the first arm and a second mounting means including a fourth arm angled and extending from the second arm, the fourth angled arm ending with a second part lying substantially parallel to the second arm, the first and second parts adapted to lie on an opposing second side of the user's leg;

said first part having a first attachment point and said second part having a second attachment point; and a first flexible strap extending from said first attachment point to said second arm and a second flexible strap extending from said second attachment point to said first arm, said first and second straps being behind the knee of the user during use;

wherein said first attachment point being spaced from said first arm and said second attachment point being spaced from said second arm, said first attachment and said second attachment remain at substantially constant distance from a selected point between the first and second attachment points during rotation of the hinge creating a virtual hinge.

2. The brace of claim 1, wherein said first attachment point being a substantially constant distance from a pivot axis of said hinge and said second attachment point being a substantially constant distance from the pivot axis of said hinge, during rotation of said hinge.

3. The brace of claim 1, wherein said first mounting means and said first strap form substantially a spiral between said first arm and a third point of attachment on said second arm and said second mounting means and said second strap form substantially a spiral between said second arm and a fourth point of attachment on said first arm.

* * * * *